United States Patent
Lupotti

(10) Patent No.: US 10,383,542 B2
(45) Date of Patent: Aug. 20, 2019

(54) DEVICE, SYSTEM, AND METHOD FOR INTRACARDIAC DIAGNOSIS OR THERAPY WITH LOCALIZATION

(71) Applicant: St. Jude Medical, Atrial Fibrillation Division, Inc., St. Paul, MN (US)

(72) Inventor: Fermin A. Lupotti, Lake Forest, CA (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 318 days.

(21) Appl. No.: 14/206,964

(22) Filed: Mar. 12, 2014

(65) Prior Publication Data

US 2014/0275957 A1    Sep. 18, 2014

Related U.S. Application Data

(60) Provisional application No. 61/784,438, filed on Mar. 14, 2013.

(51) Int. Cl.
| | |
|---|---|
| *A61B 5/06* | (2006.01) |
| *A61B 5/00* | (2006.01) |
| *A61B 18/14* | (2006.01) |
| *A61B 34/20* | (2016.01) |

(Continued)

(52) U.S. Cl.
CPC .............. *A61B 5/062* (2013.01); *A61B 5/067* (2013.01); *A61B 5/6852* (2013.01); *A61B 18/1492* (2013.01); *A61B 34/20* (2016.02); *A61B 5/7203* (2013.01); *A61B 2018/00577* (2013.01); *A61B 2034/2048* (2016.02);

(Continued)

(58) Field of Classification Search
CPC . A61B 18/1206; A61B 34/20; A61B 18/1492; A61B 5/6852; A61B 5/067; A61B 2034/2051; A61B 2090/3784; A61B 2034/2059; A61B 2034/2048; A61B 5/7203; A61B 5/00; A61B 5/06; A61B 18/00; A61B 18/14; A61B 90/00
See application file for complete search history.

(56) References Cited

U.S. PATENT DOCUMENTS

| | | |
|---|---|---|
| 5,353,354 A | 10/1994 | Keller et al. |
| 5,876,345 A | 3/1999 | Eaton et al. |

(Continued)

FOREIGN PATENT DOCUMENTS

WO    2013/019544 A1    2/2016

OTHER PUBLICATIONS

Kabra et al. Recent trends in imaging for atrial fibrillation ablation. 2010 Indian Pacing Electrophys. J. 10:215-227.*

(Continued)

*Primary Examiner* — Baisakhi Roy
*Assistant Examiner* — Patrick M Mehl
(74) *Attorney, Agent, or Firm* — Dykema Gossett PLLC

(57) ABSTRACT

A medical system for locating a catheter distal tip within a body using a plurality electrical position sensors and a magnetic position sensor in conjunction with an acceleration sensor or rotational encoder. The system locates the catheter by using signals from the acceleration sensor or rotational encoder and magnetic sensors to compensate for positioning errors associated with electric positioning sensors.

21 Claims, 10 Drawing Sheets

(51) Int. Cl.
*A61B 18/00* (2006.01)
*A61B 90/00* (2016.01)

(52) U.S. Cl.
CPC ............... *A61B 2034/2051* (2016.02); *A61B 2034/2059* (2016.02); *A61B 2090/3784* (2016.02)

(56) References Cited

U.S. PATENT DOCUMENTS

| | | | | |
|---|---|---|---|---|
| 6,061,587 | A * | 5/2000 | Kucharczyk | A61M 31/005 600/411 |
| 6,122,538 | A * | 9/2000 | Sliwa, Jr. | A61B 8/00 324/207.14 |
| 6,611,141 | B1 * | 8/2003 | Schulz | G01C 21/165 324/207.12 |
| 7,263,397 | B2 | 8/2007 | Hauck et al. | |
| 7,386,339 | B2 | 6/2008 | Strommer et al. | |
| 7,713,210 | B2 | 5/2010 | Byrd et al. | |
| 7,818,044 | B2 * | 10/2010 | Dukesherer | A61B 5/06 600/414 |
| 7,963,925 | B1 * | 6/2011 | Schecter | A61B 5/0031 600/508 |
| 8,175,681 | B2 * | 5/2012 | Hartmann | G01S 5/0263 128/899 |
| 2007/0270686 | A1 * | 11/2007 | Ritter | A61B 5/06 600/424 |
| 2008/0146941 | A1 * | 6/2008 | Dala-Krishna | A61B 8/12 600/466 |
| 2008/0146942 | A1 | 6/2008 | Dala-Krishna | |
| 2008/0234660 | A2 | 9/2008 | Cumming et al. | |
| 2009/0030332 | A1 * | 1/2009 | Schecter | A61B 5/0031 600/508 |
| 2009/0247993 | A1 | 10/2009 | Kirschenman et al. | |
| 2010/0069834 | A1 * | 3/2010 | Schultz | A61M 25/0136 604/95.04 |
| 2010/0152590 | A1 * | 6/2010 | Moore | A61B 8/12 600/466 |
| 2010/0324552 | A1 * | 12/2010 | Kauphusman | A61B 17/12036 606/41 |
| 2011/0144510 | A1 * | 6/2011 | Ryu | A61B 5/042 600/509 |
| 2011/0184274 | A1 * | 7/2011 | Rosenberg | A61B 5/0536 600/424 |
| 2011/0264074 | A1 | 10/2011 | Tegg et al. | |
| 2012/0172867 | A1 * | 7/2012 | Ryu | A61B 18/1206 606/41 |

OTHER PUBLICATIONS

Khaykin et al. 2011 J. Interv. Card. Electrophysiol. 30:233-240.*

Fallavollita The future of cardiac mapping in Cardiac Arrythmias—New Considerations Feb. 2012—Brejo-Marquez Ed. InTech chap. 22 p. 461-478.*

Lamata et al. 2010 in "Augmented Reality" Chap.5 p. 74-98; http://www.intechopen.com/books/augmented-reality/augmented-reality-for-minimally-invasive-surgeryoverview-and-some-recent-advances.*

Reddy et al. 2004 J. Am. Coll. Cardiol. 44:2202-2213.*

Eitel, Charlotte, et al. "EnSite Velocity cardiac mapping system: a new platform for 3D mapping of cardiac arrhythmias", Expert Reviews Medical Devices, 7(2), 185-192, 2010.

* cited by examiner

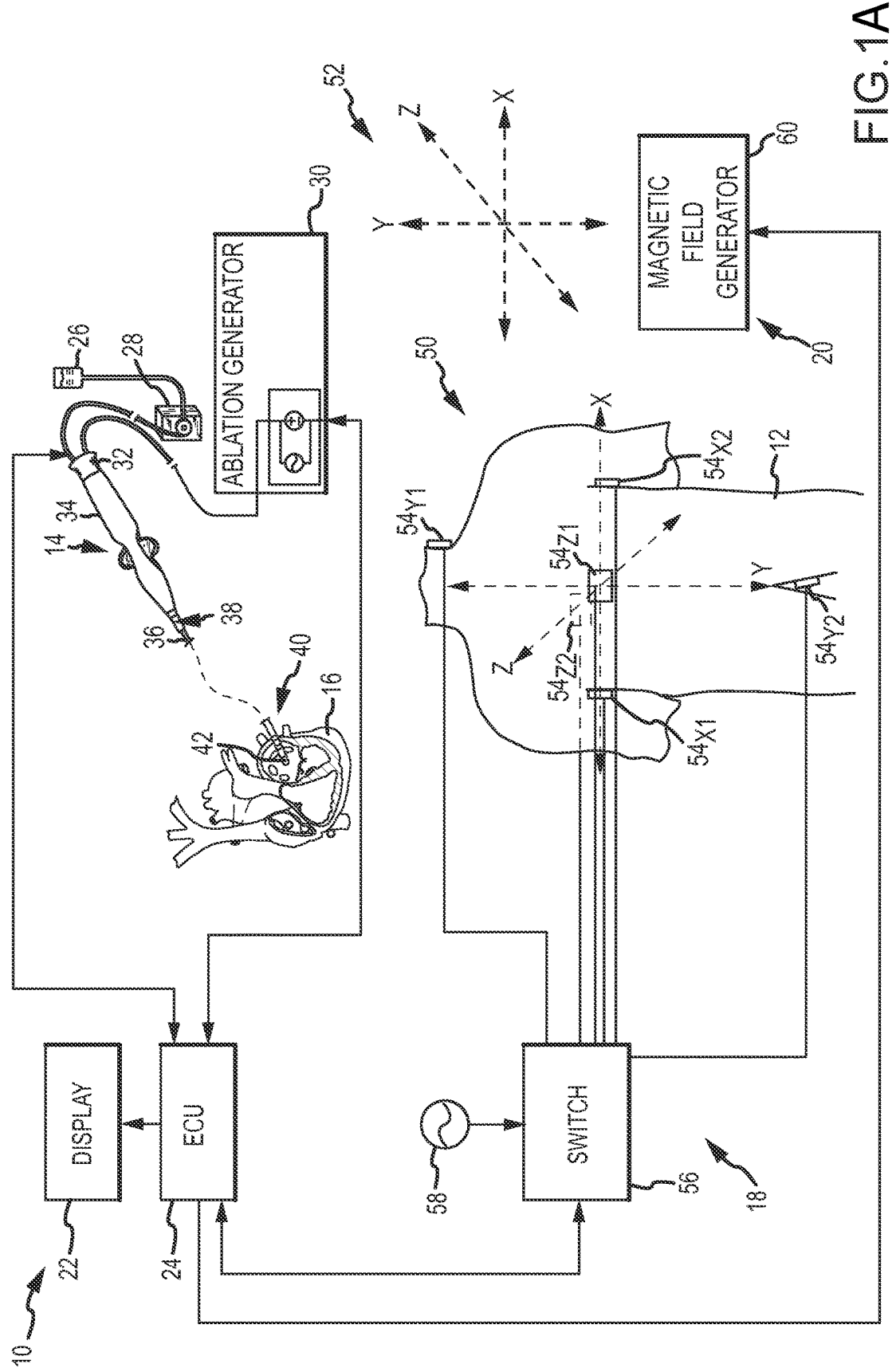

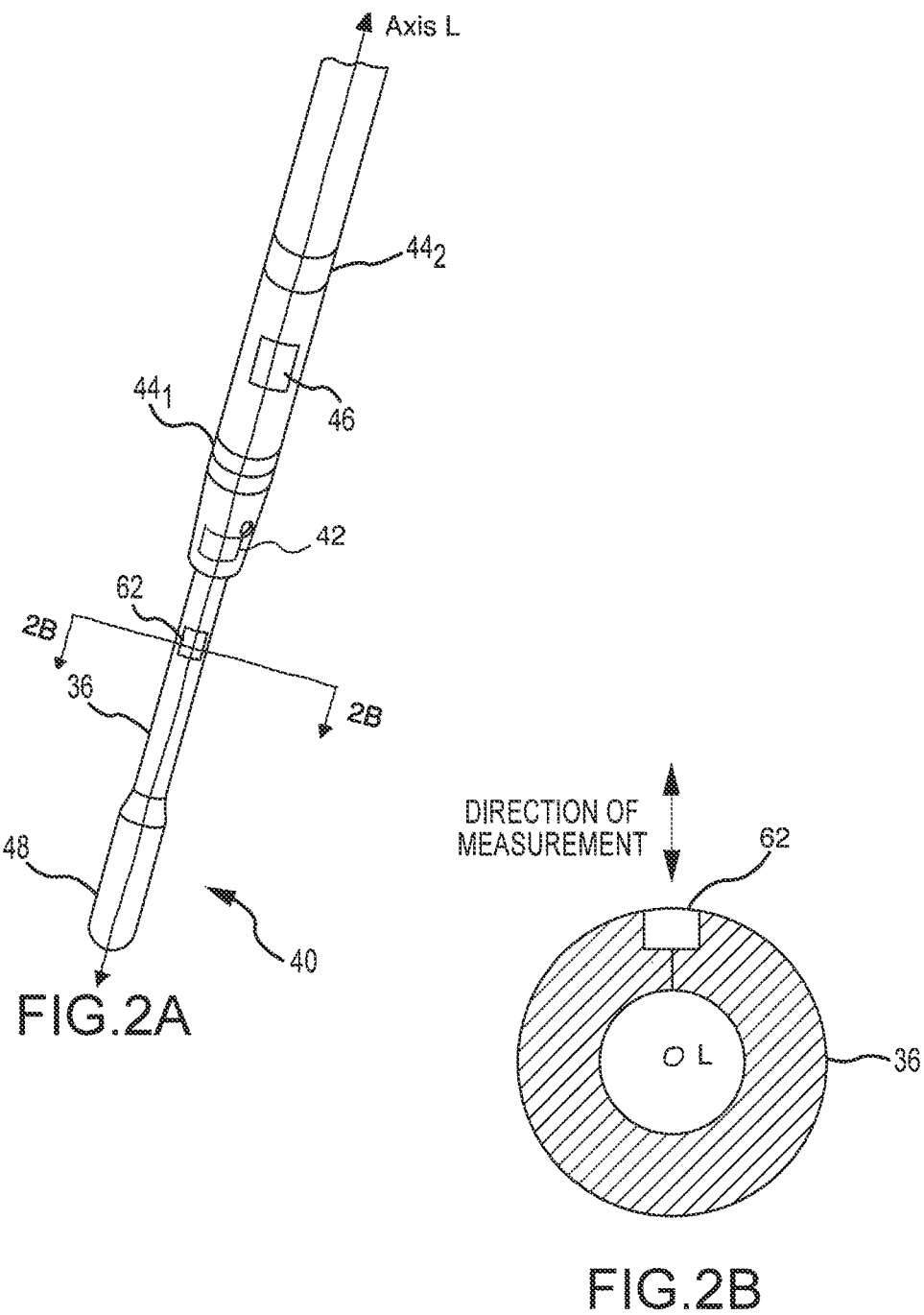

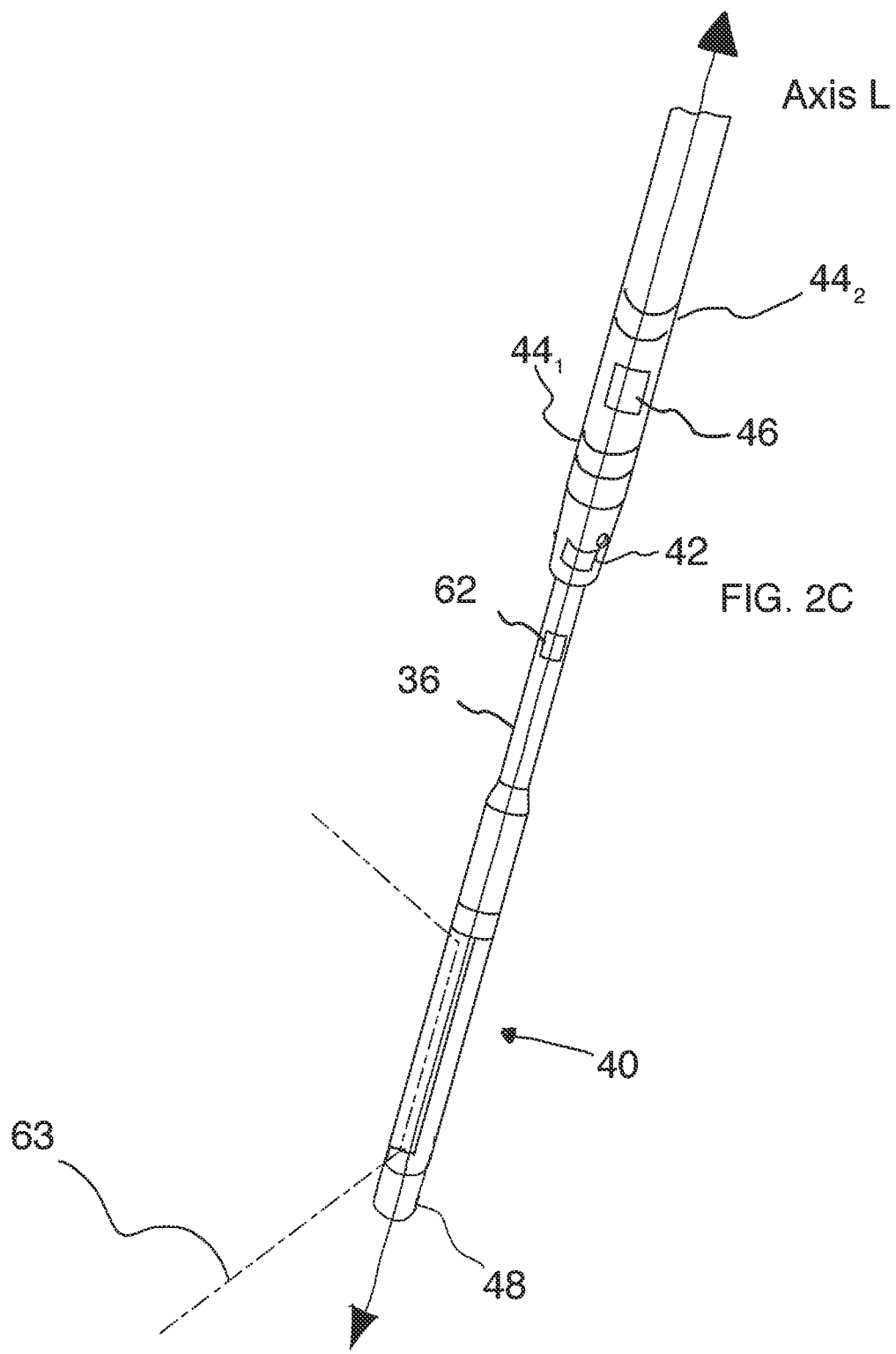

DEVICE, SYSTEM, AND METHOD FOR INTRACARDIAC DIAGNOSIS OR THERAPY WITH LOCALIZATION

BACKGROUND a. Field

The present disclosure relates to catheter location and imaging; and among other things, the present disclosure relates to devices, systems, and methods for locating, with six degrees of freedom, a catheter.

b. Background Art

Electrophysiology catheters are used in a variety of diagnostic and therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments or death.

In a typical procedure, a catheter and sheath are manipulated through a patient's vasculature to a patient's heart. In a conventional approach, an introducer is used to puncture the skin surface and a sheath having an inner diameter greater than the outer diameter of the catheter is threaded through the vasculature to a region of interest. The catheter is then moved longitudinally through the sheath to the region of interest either manually by a clinician or through the use of electromechanical drive systems. The catheter carries one or more electrodes which may be used for mapping, ablation, or other treatments. Once positioned, treatment may include radio frequency (RF) ablation, cryoablations, lasers, chemicals, high-intensity focused ultrasound, etc. An ablation catheter imparts energy to the cardiac tissue to create a lesion that disrupts undesirable electrical pathways, thereby limiting or preventing stray electric signals leading to arrhythmias. The position of the ablation catheter within the heart can directly affect the physician's ability to accurately and effectively perform an ablation procedure.

Two catheter based imaging modalities are commonly used in electrophysiology procedures, the first being intracardiac echocardiography ("ICE") that produces an ultrasound or "echo" image displaying structures within an echo plane emitted from a transducer in a catheter. Traditionally, ICE catheter orientation and position are determined by a physician with reference to landmark structures visible in the echo image in conjunction with other imaging modalities such as fluoroscopy, magnetic resonance imaging ("MRI"), or computed tomography ("CT") models.

BRIEF SUMMARY

One advantage of the apparatus, system, and method described, depicted and claimed herein relates to the reliable location and orientation of a catheter within the body.

In various embodiments, a catheter for use in the body comprises an elongate member comprising a distal portion and a proximal portion. The distal portion of the elongate member comprises a plurality of sensors, where the plurality of sensors comprises an acceleration sensor, a plurality of electrical position sensors, and a magnetic position sensor. The catheter is further comprised of a control handle attached to the proximal portion of the elongate member. The control handle comprises a deflection knob configured to deflect the distal portion of the elongate member. The sensors of the catheter are configured to generate signals such that an electronic control unit may determine a position and orientation of the distal portion in space utilizing the signals of the electrical position sensors, the magnetic position sensor, and the acceleration sensor. In various embodiments of the catheter, the distal portion can further comprise an ultrasound transducer or an ablation electrode. In various embodiments, the acceleration sensor may comprise an accelerometer that may, in some embodiments, be disposed to measure radial acceleration of the elongate member. In various embodiments, the handle may further comprise a rotational encoder configured to generate a signal, and the rotational encoder signal and the magnetic position sensor signal may be utilized in some embodiments by an electronic control unit to determine the position and orientation of the distal portion in space.

In various embodiments, a system for navigating a medical device in the body comprises an electronic control unit configured to receive a signal form an acceleration sensor located in a distal portion of a catheter, to receive a signal from a magnetic position sensor located in the distal portion of the catheter, to receive a signal from each of a plurality of electric position sensors located in the distal portion of the catheter, to control a magnetic field generator configured to generate magnetic fields in the body, and to control an electric signal generator configured to generate voltage differentials between one or more electrode patches. The electronic control unit may be further configured to generate a user interface and to control a display unit to display the interface. The electronic control unit may further be configured to determine the position and orientation of a distal portion of the catheter utilizing the signals of the electric position sensors, the magnetic position sensor, and the acceleration sensor. In various embodiments, the catheter may comprise an elongate member comprising the distal portion and a proximal portion. The catheter may further comprise a control handle attached to the proximal portion of the elongate member, and the handle may comprise a deflection knob configured to deflect the distal portion of the elongate member. In various embodiments, the electronic control unit may be further configured to control an ultrasound console, and the catheter of the system may further comprise an ultrasound transducer in communication with the ultrasound console. The ultrasound console may be configured to generate ultrasound images using the ultrasound transducer. In various embodiments, the electronic control unit may be further configured to control an ablation energy generator in communication with an ablation electrode where the ablation electrode is disposed in the distal portion of the catheter. In various other embodiments, the handle may further comprise a rotational encoder configured to generate a signal, and the rotational encoder signal and the magnetic position sensor signal may be utilized in some embodiments by the electronic control unit to determine the position and orientation of the distal portion in space. In further various embodiments, the electronic control unit may be further configured to register one or more baseline positions, to compare a position determined from electric sensors signals with a position determined from the magnetic sensor and rotational encoder signals to correct the position and orientation of the distal portion based on the comparison, or both.

In various embodiments, a method of locating a catheter in a body comprises the steps of acquiring a signal from an acceleration sensor located in a distal portion of the catheter; acquiring a signal from a magnetic position sensor located in the distal portion of the catheter; acquiring a signal from a plurality of electrical position sensors located in the distal portion of the catheter; and determining a position and orientation of the distal portion of the catheter utilizing the signals of the electrical position sensors, the magnetic position sensor and the acceleration sensor. In various embodiments the method may further comprise the steps of determining a first position and orientation from the acceleration sensor and magnetic position sensor signals, and determining a second position and orientation from the electrical position sensor signals, then comparing the first position and orientation and the second position and orientation, and correcting the position and orientation of the distal portion based on the comparison.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 1A generally illustrates a system for navigating a medical device within a body.

FIG. 2A generally illustrates the distal portion of a catheter in accordance with an embodiment of the present disclosure.

FIG. 2B generally illustrates a cross sectional view of the distal portion of the catheter illustrated in FIG. 2A, taken along line 2B-2B.

FIG. 2C generally illustrates the distal portion of a catheter in accordance with an embodiment of the present disclosure with an intracardiac echocardiography ultrasound sensor located therein.

DETAILED DESCRIPTION

Figure 1B:
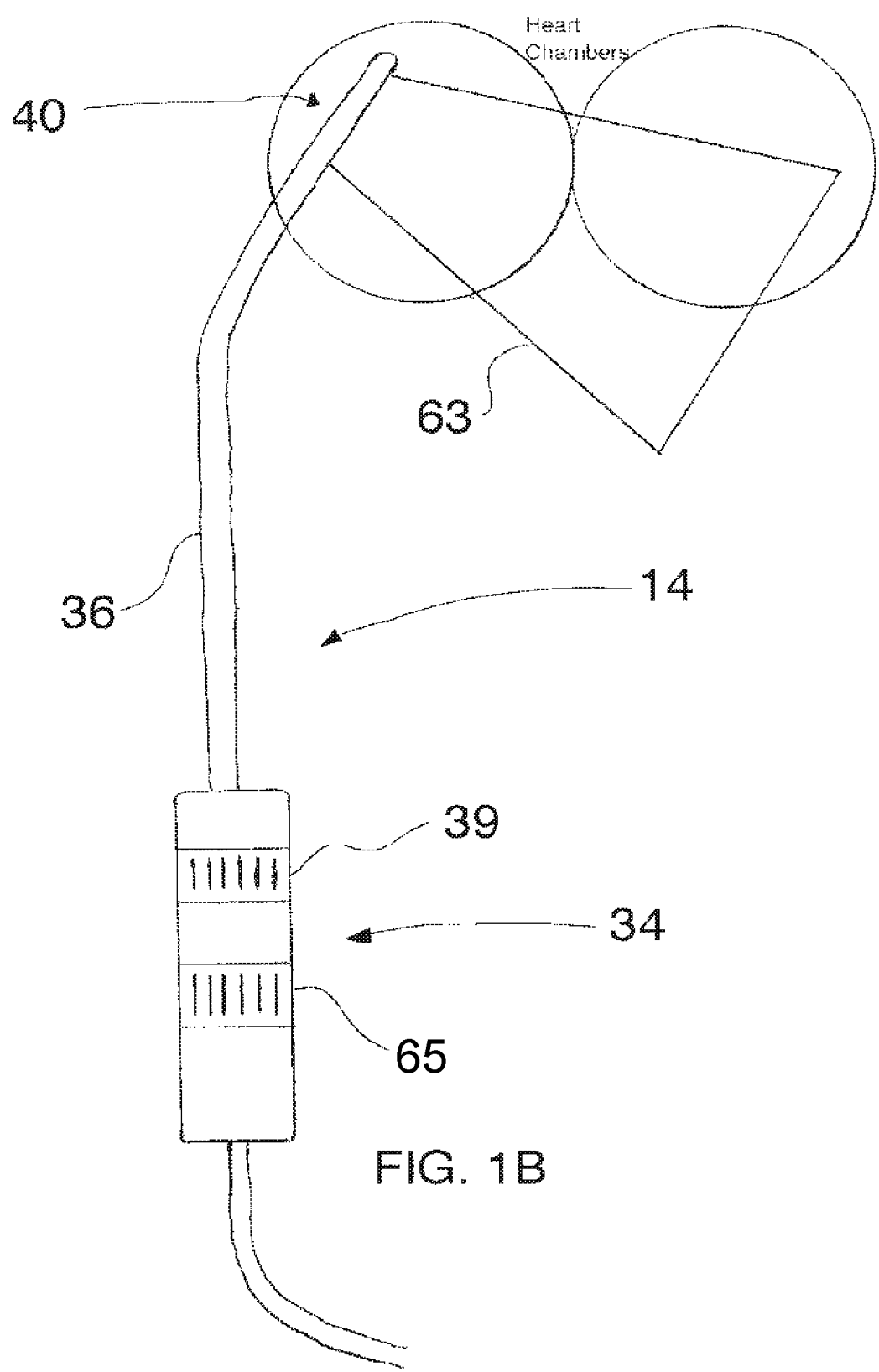
FIG. 1B schematically illustrates an intracardiac echocardiography catheter and its imaging plane.

It is desirable to track the position of medical devices such as catheters as they are moved within the body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and physician to undesirable levels of electromagnetic radiation and it is a planar projection of a 3D object like the human body and its organs. As a result, medical device navigation systems have been developed to track the position of medical devices within the body. These systems typically rely on the generation of electrical or magnetic fields and the detection of induced voltages and currents on position sensors attached to the medical device and/or external to the body. The information derived from these systems is then provided to a physician through, for example, a visual display.

One medical device navigation system is made available under the trademark "ENSITE NAVX" by St. Jude Medical, Inc. The system is based on the principle that when electrical currents are passed through the thorax a voltage drop occurs across internal organs such as the heart, and this voltage drop can be measured and used to determine the position of a medical device within the body. The system includes three pairs of patch electrodes that are placed on opposed surfaces of the body (e.g., chest and back, left and right sides of the thorax, and neck and leg), forming generally orthogonal x, y, and z axes. The system also includes a reference electrode, typically placed near the abdomen, which provides a reference value and acts as the origin of the coordinate system for the navigation system. The medical device to be tracked is outfitted with electrodes strategically placed on the device. Sinusoidal currents are driven through each pair of patch electrodes and voltage measurements for one or more electrodes associated with the medical device are obtained. The measured voltages are proportional to the distance of the device electrodes from the patch electrodes. The measured voltages are compared to the potential at the reference electrode and a position of the device electrodes within the coordinate system of the navigation system is determined.

The above-described system can be used to provide an accurate indication of the position of the medical device within a body. Electric field based navigation systems, however, are subject to various types of interference that can impact the accuracy of position measurements. For example, the level of electrical impedance in the patient body is not necessarily constant. The impedance can slowly drift or even undergo transient shifts due to, for example, a change in medication or hydration level, leading to drift and/or shift in the detected position of the medical device. Various methods have been proposed to mitigate potential drift or shift including bio-impedance scaling, patch center subtraction and the use of a fixed reference catheter with a reference electrode. Bio-impedance scaling and patch center subtraction help to reduce drift and shift, but do not eliminate all cases of drift and shift. The use of a fixed reference catheter requires insertion of an additional catheter into the body thereby increasing procedure time and the risk of complications. Further, the reference catheter may become dislodged during the procedure.

A visualization, navigation, or mapping system can employ magnetic fields and electromagnetic inductance coils to supplement an electric impedance location system. Such systems utilize a magnetic field generator to create a controlled magnetic field in the area of interest. The magnetic field causes induced electric currents in electromagnetic inductance coils embedded within the therapeutic or imaging catheters. The extent of the induced effect can be used to calculate the position and orientation of the catheter within a computer model of the area of interest. The inductance coils necessary for a magnetic field based system, however, can be expensive and difficult to manufacture in packages small enough to be embedded within catheters, limiting the number of coils that can be used in each catheter. Yet, when used in a single coil configuration, the coil does not allow for rotation measurement, preventing a precise position and orientation from being determined.

Referring now to the drawings wherein like reference numerals are used to identify similar or identical components in the various views, FIG. 1A illustrates one embodiment of a system 10 for navigating a medical device within a body 12. In the illustrated embodiment, the medical device comprises a catheter 14 and, in particular, an irrigated ablation catheter for use in diagnosis or treatment of cardiac tissue 16 in body 12. It should be understood, however, that a system 10 in accordance with the present teachings may find application in connection with a wide variety of medical devices used within body 12 for diagnosis or treatment. For example, system 10 may be used to navigate an electrophysiological (EP) mapping catheter or an intracardiac echocardiography (ICE) catheter, as illustrated in FIGS. 1A, 1B, and 2C. Further, it should be understood that the system may be used to navigate medical devices used in the diagnosis or treatment of portions of body 12 other than the tissue 16. System 10 may include an electric field based positioning system 18, a magnetic field based positioning system 20, a display 22 and an electronic control unit (ECU) 24.

Catheter 14 may be provided for examination, diagnosis and/or treatment of internal body tissues such as cardiac tissue 16. In accordance with one embodiment, catheter 14 comprises an ablation catheter and, more particularly, an irrigated radio-frequency (RF) ablation catheter. It should again be understood, however, that catheter 14 is provided for illustration only and that system 10 could be adapted for use with a variety of catheters including, for example, electrophysiology mapping catheters and intracardiac echocardiograph (ICE) catheters, as well as for use with other types of ablation catheters including those providing different types of ablation energy (e.g., cryoablation, ultrasound, etc.). Catheter 14 is connected to a fluid source 26 having a biocompatible fluid such as saline through a pump 28 (which may comprise, for example, a fixed rate roller pump or variable volume syringe pump with a gravity feed supply from fluid source 26 as shown) for irrigation. Catheter 14 is also electrically connected to an ablation generator 30 for delivery of RF energy. Catheter 14 may include a cable connector or interface 32, a handle 34, a shaft 36 having a proximal portion 38 and a distal portion 40 and one or more electrodes 42. The connector 32 can provide mechanical, fluid and/or electrical connection(s) for conduits or cables extending from the pump 28 and the ablation generator 30. Connector 32 is conventional in the art and is disposed at the proximal portion 38 of catheter 14.

Handle 34 provides a location for the physician to hold catheter 14 and may further provide means for steering or guiding shaft 36 within body 12. For example, handle 34 may include a deflection knob 39 or other means to change the length of a guidewire extending through catheter 14 to distal portion 40 of shaft 36 to steer distal portion 40 and, thus, shaft 36. Handle 34 is also conventional in the art and it will be understood that the construction of handle 34 may vary.

Shaft 36 is an elongated, flexible member configured for movement within body 12. Referring to FIG. 2A, in accordance with one embodiment, catheter 14 further includes one or more electrical position sensors $44_1$, $44_2$ and one or more magnetic position sensors 46. Catheter 14 may also include other conventional components not illustrated herein such as a temperature sensor, additional electrodes, and corresponding conductors or leads. In an embodiment, shaft 36 supports electrodes 42, sensors $44_1$, $44_2$, 46, associated conductors (not shown), and possibly additional electronics used for signal processing or conditioning. Shaft 36 may also permit transport, delivery, and/or removal of fluids (including irrigation fluids and bodily fluids), medicines, and/or surgical tools or instruments. Shaft 36 may be made from conventional materials such as polyurethane and may define one or more lumens configured to house and/or transport electrical conductors, fluids, or surgical tools. Shaft 36 may be introduced into a blood vessel or other structure within body 12 through a conventional introducer sheath. Shaft 36 may then be steered or guided through body 12 to a desired location such as tissue 16 using guide wires or pullwires, such as a guiding catheter, or other means known in the art including remote control guidance systems. One exemplary guiding catheter is described in U.S. patent application Ser. No. 11/647,313 (published as U.S. Pat. Pub. No. US2008/0234660 A1), the entire disclosure of which is incorporated herein by reference. An exemplary embodiment of a remote control guidance system is described in U.S. patent application Ser. No. 12/347,811 (published as U.S. Pat. Pub. No. US2009/0247993 A1), the entire disclosure of which is incorporated herein by reference.

Electrodes 42 may be provided for a variety of diagnostic and therapeutic purposes including, for example, electrophysiological studies, catheter identification and location, pacing, and cardiac mapping and ablation. Referring to FIG. 2A, in the illustrated embodiment, catheter 14 includes an ablation tip electrode 48 at distal portion 40 of shaft 36. It should be understood, however, that the number, orientation, and purpose of electrodes 42 may vary.

Electrical position sensors $44_1$, $44_2$ are provided for use in determining the position of catheter 14 within body 12. Sensors $44_1$, $44_2$ are conventional in the art. In the illustrated embodiment, sensors $44_1$, $44_2$ comprise electrodes and, in particular, conventional ring electrodes located proximal to the distal portion 40 of catheter shaft 36 and tip electrode 48. As sensors $44_1$, $44_2$ move within body 14, and within the electric field generated by system 18, the voltage readings from sensors $44_1$, $44_2$ change, thereby indicating the location of sensors $44_1$, $44_2$ within the electric field and with a coordinate system 50 established by system 18. Sensors $44_1$, $44_2$ communicate position signals to ECU 24 through a conventional interface (not shown).

Electric field based positioning system 18 is provided to determine the position and orientation of catheter 14 and similar devices within body 12. System 18 may comprise the system made available under the trademark "ENSITE NAVX" by St. Jude Medical, Inc. and described, for example, in U.S. Pat. No. 7,263,397" the entire disclosure of which is incorporated herein by reference. The system is based on the principle that when low amplitude electrical signals are passed through the thorax, body 12 acts as a voltage divider (or potentiometer or rheostat) such that the electrical potential or field strength measured at an electrode such as one of position sensors $44_1$, $44_2$ on catheter 14 may be used to determine the position of the electrode, and therefore catheter 14, relative to a pair of external patch electrodes using Ohm's law and the relative location of a reference electrode (e.g. in the coronary sinus). In one configuration, the system includes three pairs of patch electrodes 54 that are placed on opposed surfaces of body 12 (e.g., chest and back, left and right sides of the thorax, and neck and leg), which form generally orthogonal x, y, and z axes. A reference electrode/patch (not shown) that is typically placed near the abdomen provides a reference value and acts as the origin of the coordinate system 50 for the navigation system. Sinusoidal currents are driven through each pair of patch electrodes 54 and voltage measurements for one or more position sensors $44_1$, $44_2$ associated with catheter 14 are obtained. The measured voltages are a function of the distance of the position sensors 44$_1$, 44$_2$ from the patch electrodes 54. The measured voltages are compared to the potential at the reference electrode and the position of sensors 44$_1$, 44$_2$ within the coordinate system 50 of the navigation system is determined. In accordance with this exemplary system, system 18 may include patch electrodes 54 (namely 54$_{X1}$, 54$_{X2}$, 54$_{Y1}$, 54$_{Y2}$, 54$_{Z1}$, 54$_{Z2}$) a switch 56, and a signal generator 58.

Patch electrodes 54 are provided to generate electrical signals used in determining the position of catheter 14 within three-dimensional coordinate system 50 of system 18. Electrodes 54 may also be used to generate EP data regarding tissue 16. Electrodes 54 are placed orthogonally on the surface of body 12 and are used to create axes specific electric fields within body 12. Electrodes 54$_{X1}$, 54$_{X2}$ may be placed along a first (x) axis. Similarly, electrodes 54$_{Y1}$, 54$_{Y2}$ may be placed along a second (y) axis, and electrodes 54$_{Z1}$, 54$_{Z2}$ may be placed along a third (z) axis. Each of the electrodes 54 may be coupled to multiplex switch 56. ECU 24 is configured through appropriate software to provide control signals to switch 56 and thereby sequentially couple pairs of electrodes 54 to signal generator 58. Excitation of each pair of electrodes 54 generates an electromagnetic field within body 14 and within an area of interest such as the heart. Voltage levels at non-excited electrodes 54 may be filtered and converted and provided to ECU 24 for use as reference values.

Magnetic position sensors 46 are also provided for use in determining the position of catheter 14 within body 12. Sensors 46 are conventional in the art. In the illustrated embodiment, sensors 46 are coils. As sensors 46 move within body 14, and within the magnetic field generated by system 20, the current output of each sensor 46 changes thereby indicating the location of sensors 46 within the magnetic field and within a coordinate system 52 established by system 20. Sensors 46 may be wound about catheter 14 at or near distal portion 40 and may be embedded within the walls of catheter 14 such that sensors 46 are insulated. Alternatively, sensors 46 could be embedded further within catheter 14 as shown in FIG. 2A, or could be placed at other locations within the catheter 14. Sensors 46 may also have appropriate insulation and/or shielding (e.g., a conductive foil or wire mesh) to cancel potential interferences from other devices near body 12. It should be understood that sensors 46 may take forms other than the form illustrated in FIG. 2A. Sensors 46 may, for example, comprise any conventional position sensors for detecting changes in magnetic fields including Hall effect sensors, magnetoresistive sensors and sensors made from magnetoresistive materials and piezoelectric materials and the like. Sensors 46 communicate position signals to ECU 24 through a conventional interface (not shown). In accordance with one aspect of the present teachings, each of magnetic position sensors 46 is disposed proximate to a corresponding electrical position sensor 44$_1$, 44$_2$ such that the detected position of one of sensors 44, 46 may be indicative of the position of the other corresponding sensor 44, 46. The magnetic position sensors 46 may, for example be located from about 1.0 to about 3.0 millimeters from a corresponding electrical position sensor 44$_1$, 44$_2$ and may be centered between two electrical position sensors 44$_1$, 44$_2$ which may be spaced about 2.0 to 6.0 millimeters apart.

System 20 may also determine the position and orientation of catheter 14 and similar devices within body 12. System 20 comprises a system that employs magnetic fields to detect the position of catheter 14 within body 12 such as the system made available under the trademark "MEDI-GUIDE" by St. Jude Medical, Inc. and generally shown and described in, for example, U.S. Pat. No. 7,386,339" the entire disclosure of which is incorporated herein by reference. In such a system, a magnetic field generator 60 may be employed having orthogonally arranged coils that create a magnetic field within body 12 and controls the strength, orientation, and frequency of the field. The magnetic field generator 60 may be located above or below the patient (e.g., under a patient table) or in another appropriate location. Magnetic fields are generated by the coils and current or voltage measurements for one or more position sensors 46 associated with catheter 14 are obtained. The measured currents or voltages are proportional to the distance of the sensors 46 from the coils thereby allowing a position of the sensors 46 within a coordinate system 52 of system 20.

System 20 may also determine the position and orientation of catheter 14 and similar devices within body 12 using a single magnetic position sensor 46 and an acceleration sensor 62. Use of an accelerometer allows the position and orientation of the catheter to be determined using only a single magnetic field sensor 46. A typical magnetic field sensor 46 cannot by itself be used to detect six degrees of freedom because it cannot detect roll about the sensor's longitudinal axis. The acceleration sensor 62 remedies this deficiency by allowing the ECU 24 to calculate the roll about the longitudinal axis L (see FIGS. 2A-2C) when the catheter accelerates about that axis. Compensation for roll about axis L is described in more detail below. Reducing the number of magnetic field sensors 46 allows the catheter to have a smaller physical form while still maintaining the ability to locate the device precisely. The acceleration sensor 62 communicates signals to ECU 24 through a conventional interface (not shown). In accordance with one aspect of the present teachings, the acceleration sensor 62 is disposed in the proximal portion 38 of shaft 36. The signal generated by the acceleration sensor 62 can be used by ECU 24 to determine the amount of axial rotational of the shaft 36.

The ability to accurately measure the rotational position or roll of shaft 36 is important when utilizing an ICE catheter, as illustrated in FIGS. 1B and 2C, because it allows a more precise location of echo images from ICE catheters to be determined. ICE catheters produce an image using data collected from an imaging plane 63 extending perpendicular to the longitudinal axis L. The perpendicular nature of the imaging plane 63 causes small angular orientation errors to be translated into translational errors that grow proportionally larger as the distance from the shaft 36 grows larger. Therefore, determining the rotation or roll position accurately, as described in more detail below, allows the ICE image to be more precisely located within the body.

As illustrated in FIGS. 2A and 2B, acceleration sensor 62 can comprise a single accelerometer positioned on the outer diameter of the catheter body that is oriented to measure acceleration of shaft 36 in a radial direction. In this position and orientation, rotation of the shaft 36 causes a radial acceleration toward the catheter central axis proportional to the instantaneous angular velocity. The ECU 24 can distinguish a rotational movement from a translational movement in the accelerometer's axial direction using the position signal from the magnetic field sensor 46. The position signal of the magnetic field sensor 46 should not change with an axial rotation, as the magnetic field sensor's 46 position in the magnetic field is unchanged when the coil itself is merely rotated within the field. More specifically, rotation of a circular coil occupying the x-y plane about an axis in the z plane extending through the circle's midpoint causes no change in magnetic flux through the circular coil. In contrast, when a translational movement occurs, the magnetic field flux changes as the coil is moved into a stronger/weaker region of the magnetic field, thereby inducing a current in the coil. Thus, when the accelerometer registers an axial acceleration but the magnetic signal is unchanged, a rotational movement has occurred. When both a translational movement and rotational movement occur at the same time, the displacement measured by the coil must be used to correct the acceleration signal by removing acceleration associated with the translational movement. Thus, catheter tip location is measured by sensor 46 while adjusted tip orientation (rotational) is obtained by sensor 62.

In another embodiment in accordance with one aspect of the present teachings, acceleration sensor 62 includes the ability to detect acceleration in three dimensions, such as, by way of example, including three accelerometers oriented in orthogonal directions corresponding to x, y, and z axes. Each accelerometer measures the magnitude of acceleration experienced along its respective axis and produces an acceleration signal. The three acceleration signals are communicated by the acceleration sensor 62 to the ECU 24 as part of the acceleration sensor's 62 signal. The ECU 24 can use the acceleration sensor 62 signals with other position signals to calculate a change in the distal portion's 40 position and orientation.

In either of the above described embodiments a position change is determined by the ECU 24 from instantaneous acceleration measurements. A position vector can be determined from an acceleration by twice integrating the acceleration signal with respect to time. The resulting position vector represents a relative displacement from the sensor's initial position at the beginning of the integral time period. Thus, the ECU 24 requires a known baseline or initial position from which the relative position vector calculated from the signal of the acceleration sensor 62 can be applied. The initial position can be obtained at the start of the procedure using reliable position from, for example, the position generated from the position signals from the electrical position sensors 44.

Further baseline positions can be established through the comparison of the magnetic/accelerometer position against the position of the electrical position sensors. When the two positions are substantially the same displacement from the previous baseline, then the new position can be used as a new baseline position. As a procedure progresses, a series of baseline positions can be used to ensure that the relative position vector of the magnetic/accelerometer position is integrated over a small enough time frame to reduce error in the integration calculation caused by the sampling rate of the accelerometer. Higher sampling rates reduce the integration error, but require more processing power from the ECU due to the higher number of data points being integrated. Using frequent baseline positions minimizes the accumulation of integration errors, which can lead to unacceptable rotational position accuracy. Other combinations can be accelerometers and coils (rotation and position) or accelerometers and electrodes (rotation and position). In either case, location/orientation and integration errors can be minimized by increasing the sampling rate or by correcting the data between the different sensors.

Where an unacceptable discrepancy between the magnetic/accelerometer position and the electrical impedance based position is detected by the ECU, the magnetic/accelerometer position can be used until a new baseline position is established after the discrepancy is no longer detected. For persistent discrepancies, such as those occurring due to hydration changes or medication effects in the patient, a correction factor can be calculated and applied to the electrical impedance based position to account for the impedance error.

Figure 2D:
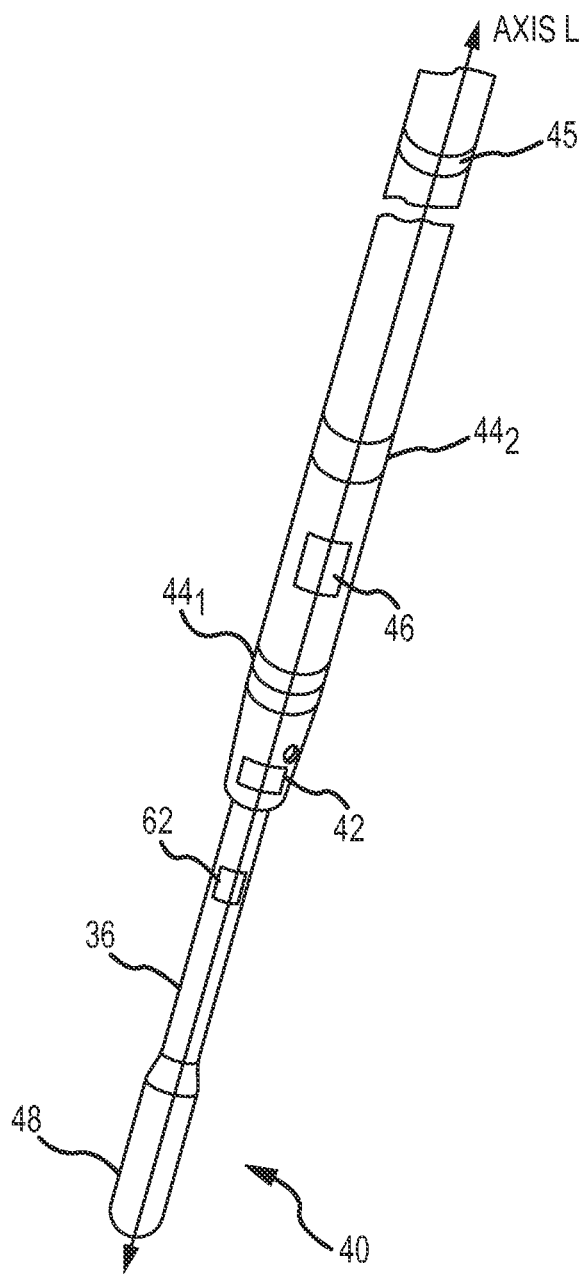
FIG. 2D generally illustrates the distal portion of a catheter in accordance with an embodiment of the present disclosure, including an additional sensor to allow for force sensing.

In another embodiment in accordance with one aspect of the present teachings, system 20 may not only determine the position and orientation of catheter 14, but also determine the force being applied to tissue by the distal tip of catheter 14. Force at the distal tip of catheter 14 can be sensed with the addition of another sensor 45 placed near (or at) the distal portion 40 of catheter 14, as shown in FIG. 2D. Sensor 45 can be a an electrical position sensor, a magnetic position sensor, or an acceleration sensor as described above, for example. By knowing the distance between sensor 45 and another sensor on shaft 36, and knowing the mechanical properties (e.g., flexibility) of the material that forms shaft 36, the force at the distal tip can be calculated. In the illustrated embodiment, magnetic field sensor 46 may be used as the reference electrode, and sensor 45 can be located about 0.3-2.0 cm distal to sensor 46. When catheter 14 comes into contact with tissue with sufficient force, the catheter may bend at the distal portion and the distance between sensors 45 and 46 may decrease. In this way, the distance between sensors 45 and 46 can be used to determine the force being applied by catheter 14. Additional details on such sensor-to-sensor distance and/or position monitoring may be found in PCT pub. no. WO 2013/019544 A1, incorporated herein by reference in its entirety.

Figure 3:
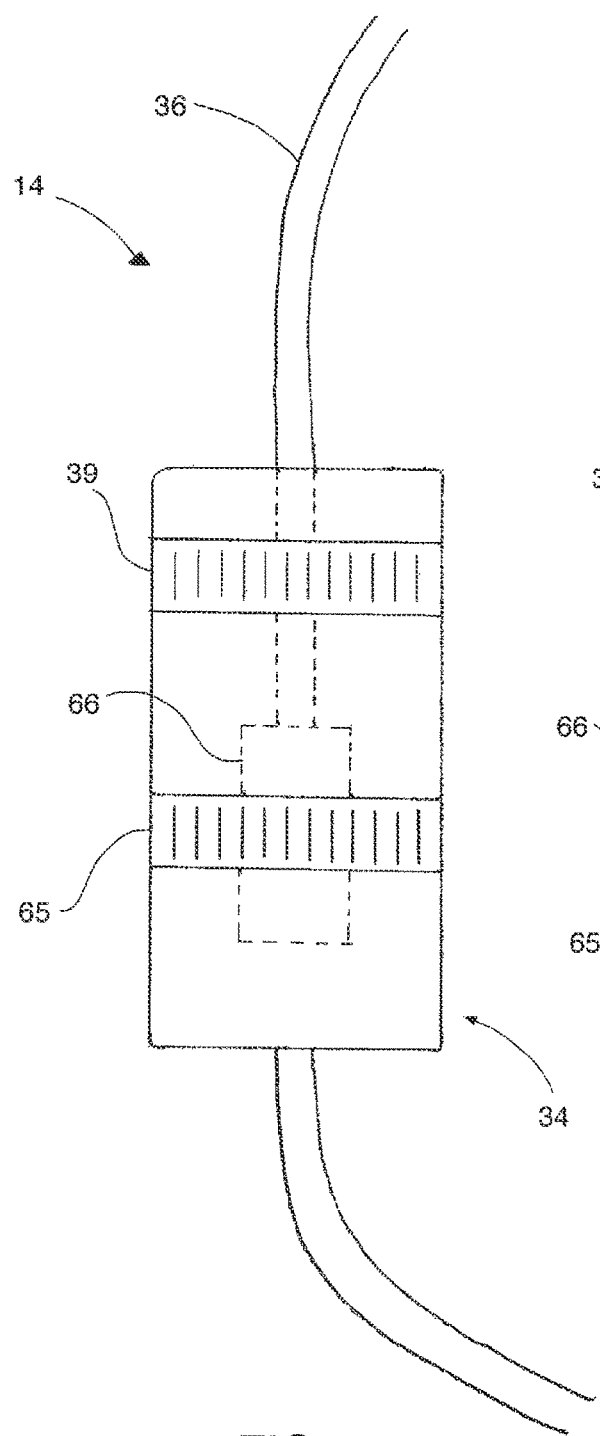
FIG. 3 is a schematic illustrating a catheter handle containing a rotational sensor in accordance with an embodiment of the present disclosure.
Figure 4:
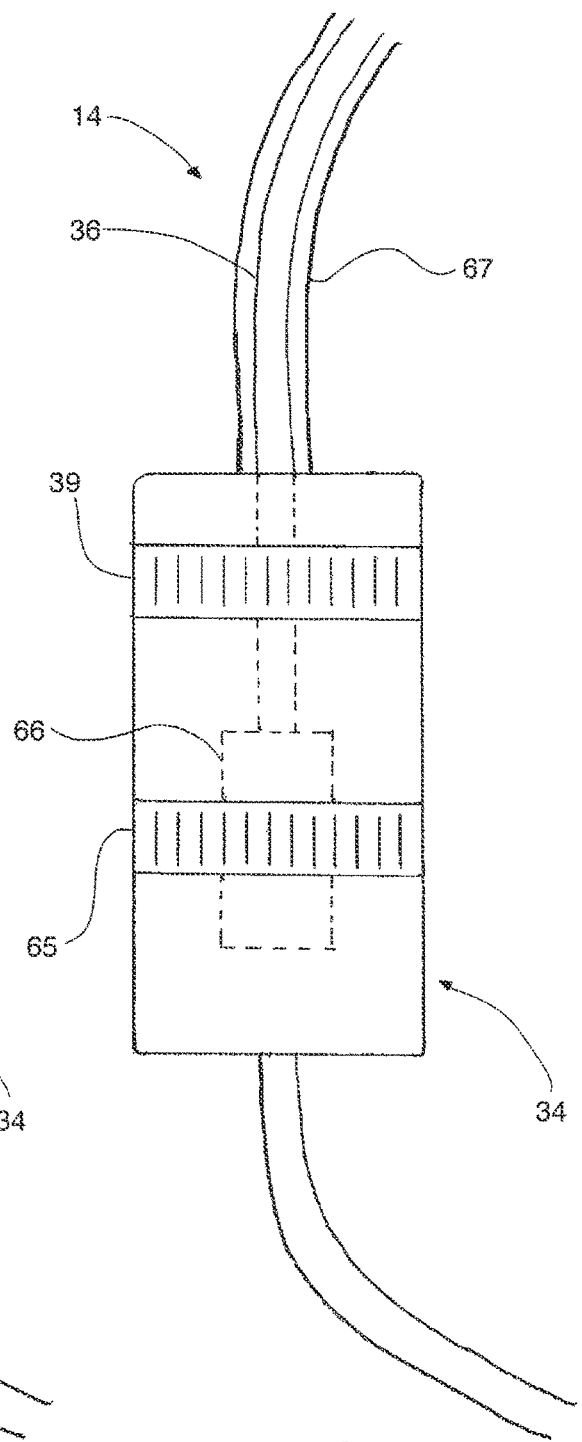
FIG. 4 is a schematic illustrating a catheter handle and an attached sheath containing a rotational sensor in accordance with an embodiment of the present disclosure.
Figure 5:
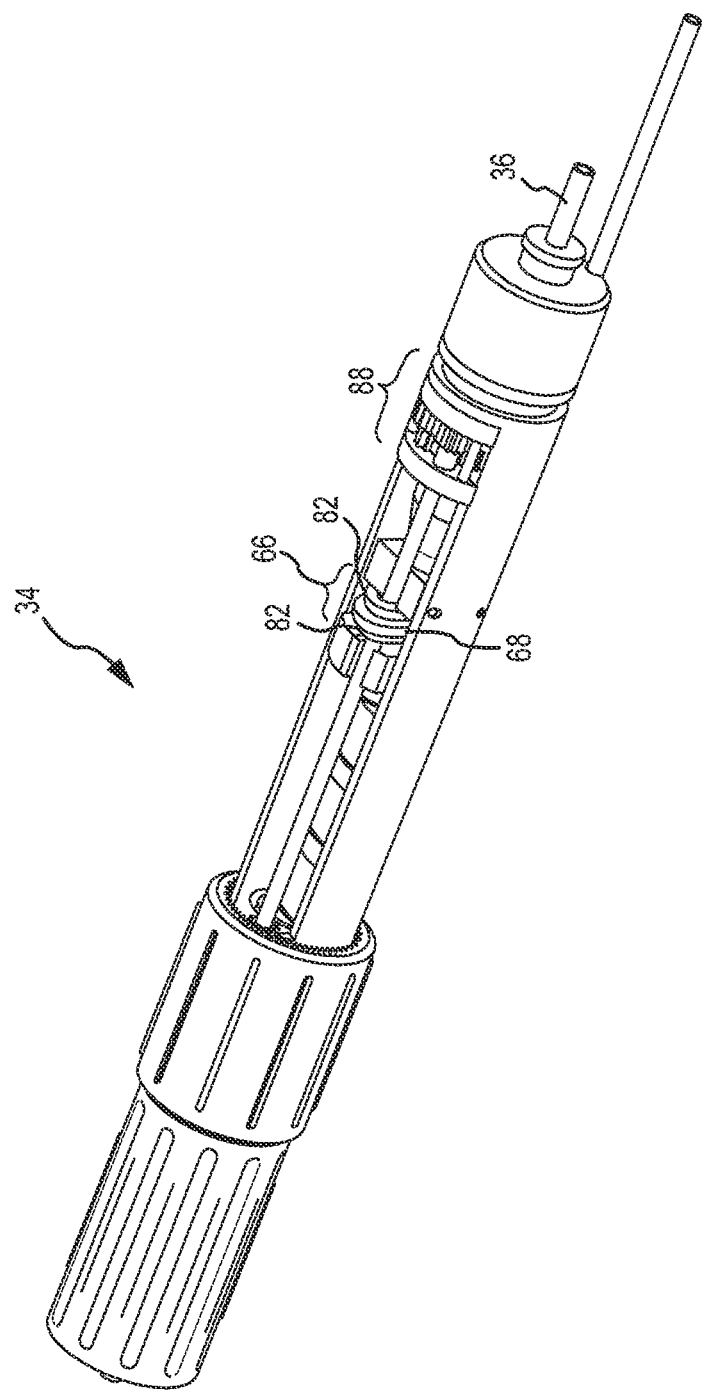
FIG. 5 generally illustrates a catheter handle containing a rotational sensor in accordance with an embodiment of the present disclosure.

In another embodiment, as illustrated in FIGS. 3-8 in accordance with one aspect of the present teachings, axial rotation of the shaft 36, controlled by a rotation knob 65 or similar actuator, can be detected using a rotation sensor 66 configured to generate a rotation position signal communicated to the ECU 24 using a conventional interface. The rotation sensor 66 detects the rotational movement of the shaft 36 relative to a fixed reference point such as the handle 34 or an attached sheath 67. As illustrated in FIGS. 3-5, the rotational sensor 66 can be disposed within handle 34 to measure the relative rotational motion between the shaft 36 and the handle 34, which acts as the fixed reference. In catheter embodiments where the shaft 36 is not rotated independent from handle 34, such as, by way of example, catheters where rotation of shaft 36 is accomplished by rotating both handle 34 and an attached shaft, the rotation sensor 66 can be disposed on the sheath or fixedly attached to the patient at the introducer site to provide the fixed reference point.

Figure 6:
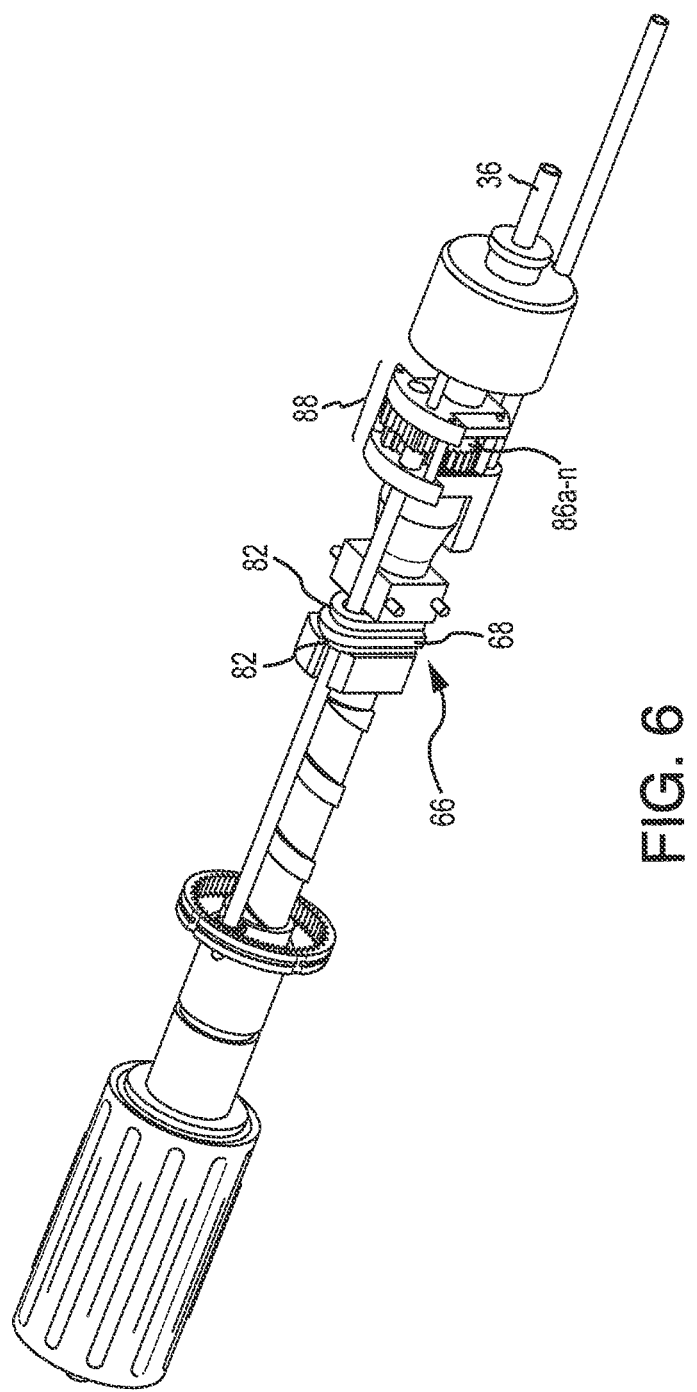
FIG. 6 is a cutaway view of the handle illustrated in FIG. 5 further illustrating the rotational sensor within the handle.
Figure 7:
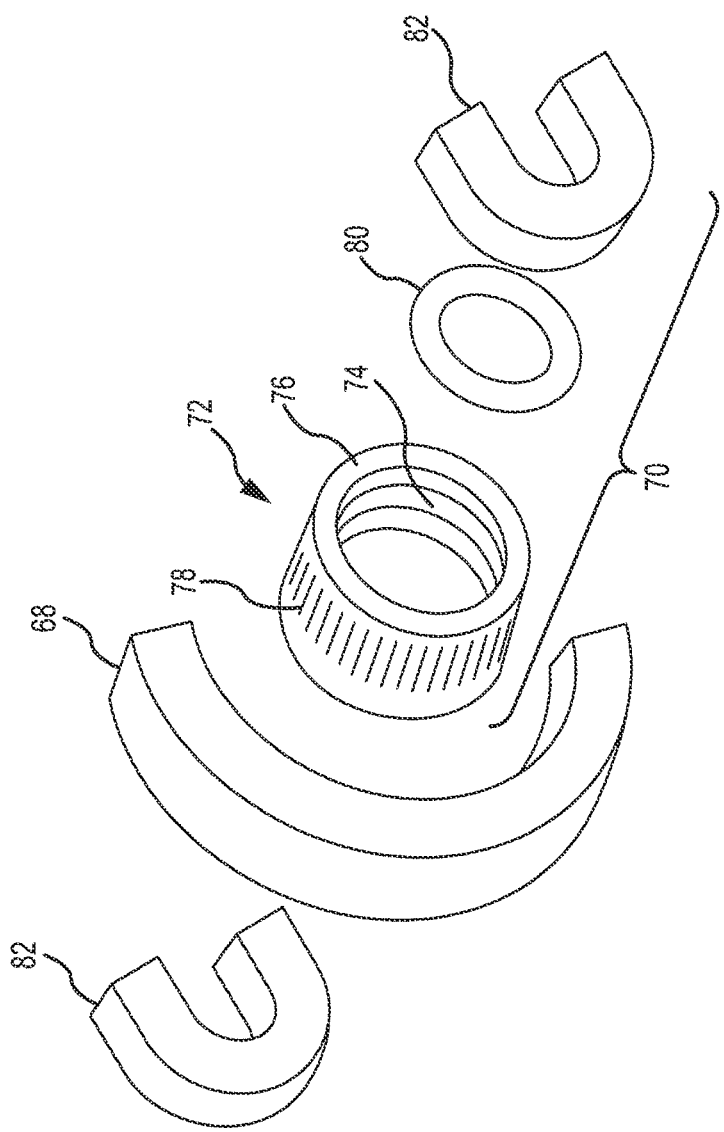
FIG. 7 is an exploded view of a rotational sensor generally illustrated in FIGS. 5 and 6.
Figure 8:
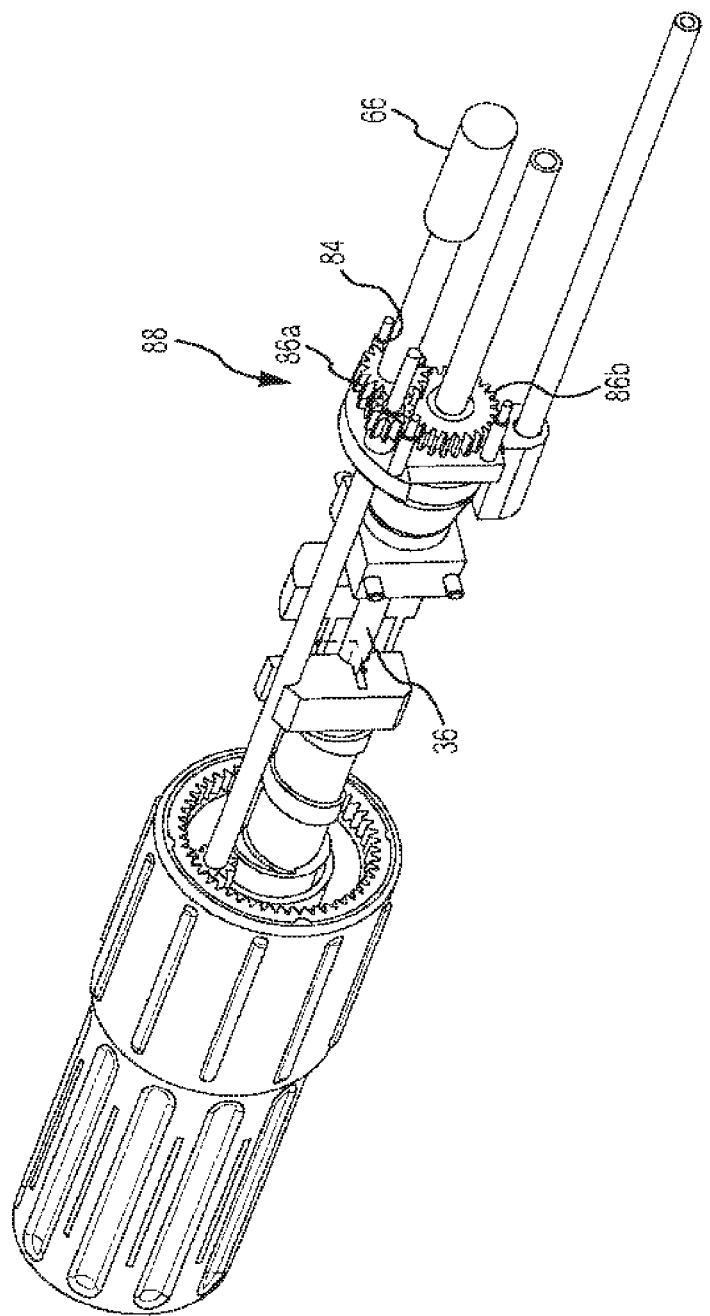
FIG. 8 is a cutaway view of a catheter handle having a rotational sensor coupled to an output shaft from a rotational gear assembly.

In another embodiment in accordance with one aspect of the present teachings, the rotational sensor 66 is disposed such that the shaft 36 can be axially advanced and retracted while the rotation sensor 66 is functioning without the rotation sensor traveling through corresponding axial movements. An example of such an embodiment is illustrated in FIGS. 5-7, where handle 34 includes a rotational sensor 66 comprising a reader portion 68 and a rotation portion 70. The rotation portion 70 comprises a ring 72 having an inner channel 74, one or more contact surfaces 76, and a graduated surface 78. A sealing ring 80 is disposed within inner channel 74 such that shaft 36 extends through the sealing ring 80 while maintaining contact with the same. The sealing ring 80 should be made from a flexible material that compresses when shaft 36 is passed through the ring 80. The sealing ring 80 should be sized such that when the ring is compressed the shaft 36 should be capable of sliding axially through the ring with the application of axial force from the clinician.

The contact surfaces 76 are substantially parallel and abut support surfaces 82 that extend from handle 34. Support surfaces 82 maintain the rotation portion 70 in a substantially fixed axial position within the handle 34 by exerting a force against the contact surfaces 76 when the shaft 36 is moved axially through sealing ring 80. For example, when shaft 36 is advanced axially in the distal direction, the support surface 82 located distal to the rotation portion 70 exerts a force against its adjacent contact surface 76, preventing rotation portion 70 from moving axially with shaft 36. When shaft 36 is retracted axially in the proximal direction, the support surface 82 located proximal to the rotation portion 70 exerts a force against its adjacent contact surface 76, preventing rotation portion 70 from moving distally with shaft 36.

Reader portion 68 is disposed within handle 34 adjacent to the graduated surface 78 of the rotation portion 70. The reader portion 68 is fixedly attached to handle 34 and remains substantially stationary during rotational movements of shaft 36. The graduated surface 78 includes a series of graduations designed to be detected by an encoder in the reader portion 68. The graduations, for example, can be alternating magnetic polarities, light and dark stripes, or varying electrical resistances for use with magnetic, optical, or electrical encoders, respectively. Rotational encoders can be configured to provide relative, i.e. incremental, rotational movements by using graduations having only alternating, i.e., binary, encoding, or absolute rotational position using a graduations that include additional coding. Both relative and absolute encoder/graduation pairs can be utilized to provide rotational position signals described herein.

In another embodiment in accordance with one aspect of the present teachings, the rotational sensor 66 can be coupled to a rotational gear assembly within handle 34 of the type described in U.S. patent application Ser. No. 13/107, 583 (published as United States patent application publication no. US 2011/0264074 A1) which is herein incorporated by reference in its entirety. In this embodiment, illustrated generally in FIG. 8, the rotational sensor 66 can be a traditional rotatory encoder fixedly attached within handle 34 that is coupled to an output shaft 84 extending from one of n number of gears 86a-n in the rotational gear assembly 88. As the gears 86a-n in the rotational gear assembly 88 rotate to turn the shaft 36, the output shaft 84 rotates in proportion to the gear ratio between the gear 86a to which it is attached and the gear 86b through which shaft 36 runs.

Although several embodiments have been described above with a certain degree of particularity, those skilled in the art could make numerous alterations to the disclosed embodiments without departing from the spirit or scope of this disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It should be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter for use in a body, the catheter comprising:
an elongate member comprising a distal portion and a proximal portion;
the distal portion comprising a plurality of sensors, the plurality of sensors comprising an acceleration sensor, a plurality of electrical position sensors configured to produce a first signal indicative of five degrees of freedom of the distal portion, and a magnetic position sensor configured to produce a second signal indicative of the five degrees of freedom of the distal portion; and
a control handle attached to the proximal portion of the elongate member, the control handle comprising a deflection knob configured to deflect the distal portion of the elongate member;
wherein the sensors are configured to generate a set of first signals, the set of first signals being collectively indicative of a position and an orientation of the distal portion in space; and
wherein the acceleration sensor is configured to produce a third signal indicative of a sixth degree of freedom of the distal portion.

2. The catheter of claim 1, the distal portion further comprising an ultrasound transducer; and wherein the position and orientation of the distal portion in space includes all six degrees of freedom.

3. The catheter of claim 1, the distal portion further comprising an ablation electrode; and wherein the magnetic position sensor is parallel to a longitudinal axis of the catheter.

4. The catheter of claim 1, wherein the acceleration sensor further comprises an accelerometer; and wherein the sixth degree of freedom is a rotation along a longitudinal axis of the elongated member.

5. The catheter of claim 4, the accelerometer being disposed to measure radial acceleration of the elongate member.

6. The catheter of claim 1, the acceleration sensor further comprising orthogonally oriented accelerometers.

7. The catheter of claim 1, the handle further comprising a rotational encoder configured to generate at least one second signal.

8. The catheter of claim 7, wherein the second signal of the rotational encoder and the first signal of the magnetic position sensor are to determine the position and orientation of the distal portion in space.

9. A system for navigating a medical device in a body comprising:
an electronic control unit, the electronic control unit being configured to:
receive a first signal from an acceleration sensor located in a distal portion of a catheter, the first signal indicative of a sixth degree of freedom of a position and orientation of the distal portion;
receive a second signal from a magnetic position sensor located in the distal portion of the catheter, the second signal indicative of five degrees of freedom of the distal portion;
receive a third signal from each of a plurality of electric position sensors located in the distal portion of the catheter, the third signal indicative of the five degrees of freedom of the distal portion;
determine a position and an orientation of the distal portion of the catheter utilizing the third signal of the electric position sensors and the second signal of the magnetic position sensor to determine five degrees of freedom of the distal portion, and the first signal of the acceleration sensor to determine the sixth degree of freedom of the distal portion;
control a magnetic field generator configured to generate magnetic fields in the body;
control an electric signal generator configured to generate voltage differentials between one or more electrode patches;
generate a user interface; and
control a display unit to display the interface.

10. The system of claim 9, wherein the catheter comprises:
an elongate member comprising the distal portion and a proximal portion; and
a control handle attached to the proximal portion of the elongate member, the control handle comprising a deflection knob configured to deflect the distal portion of the elongate member.

11. The system of claim 10, the handle further having a rotational encoder configured to generate a signal.

12. The system of claim 11, the electronic control unit being further configured to determine the position and orientation of the distal portion of the catheter in space utilizing the signals of the rotational encoder and the magnetic position sensor.

13. The system of claim 11, wherein the electronic control unit is further configured to register one or more baseline positions.

14. The system of claim 13, wherein the electronic control unit is configured to compare a position determined from the electric sensors signals to a position determined from the magnetic sensor and the rotational encoder signals and to correct the position and orientation of the distal portion of the catheter based on the comparison.

15. The system of claim 9, the electronic control unit further being configured to control an ultrasound console, and the distal portion further comprising an ultrasound transducer in communication with the ultrasound console; the ultrasound console being configured to generate ultrasound images using the ultrasound transducer.

16. The system of claim 9, the electronic control unit further being configured to control an ablation energy generator in communication with an ablation electrode, the distal portion further comprising the ablation electrode; and wherein the sixth degree of freedom is a rotation along a longitudinal axis of the medical device.

17. The system of claim 9, wherein the acceleration sensor further comprises an accelerometer; and wherein the magnetic position sensor and the plurality of electric positions cannot detect motion of the medical device in the sixth degree of freedom.

18. The system of claim 17, the accelerometer being disposed to measure radial acceleration of the flexible member.

19. The system of claim 17, the acceleration sensor further comprising orthogonally oriented accelerometers.

20. A method of locating a catheter within a body, the method comprising the steps of:
acquiring a first signal from an acceleration sensor located in a distal portion of the catheter, the first signal indicative of a sixth degree of freedom of a position and orientation of the distal portion;
acquiring a second signal from a magnetic position sensor located in the distal portion of the catheter, the second signal indicative of five degrees of freedom of the distal portion;
acquiring a third signal from each of a plurality of electrical position sensors located in the distal portion of the catheter, the third signal indicative of the five degrees of freedom of a position and orientation of the distal portion; and
determining a position and orientation of the distal portion of the catheter utilizing the signals of the electrical position sensors, the magnetic position sensor and the acceleration sensor.

21. The method of claim 20, further comprising the steps of:
determining a first position and orientation from the acceleration sensor and magnetic position sensor signals;
determining a second position and orientation from the electrical position sensor signals;
comparing the first position and orientation and the second position and orientation; and
correcting the position and orientation of the distal portion based on the comparison.

* * * * *